United States Patent [19]
Hickmann et al.

[11] 4,327,215
[45] Apr. 27, 1982

[54] PREPARATION OF ERYTHRO-α-PIPERID-2-yl-2,8-BIS-(TRIFLUORO-METHYL)-QUINOLIN-4-yl METHANOL

[75] Inventors: Eckhard Hickmann; Heinz-Guenter Oeser, both of Ludwigshafen; Leander Moebius, Erpolzheim, all of Fed. Rep. of Germany

[73] Assignee: BASF Aktiengesellschaft, Fed. Rep. of Germany

[21] Appl. No.: 193,473

[22] Filed: Oct. 3, 1980

[30] Foreign Application Priority Data

Oct. 5, 1979 [DE] Fed. Rep. of Germany ....... 2940443

[51] Int. Cl.$^3$ .......................................... C07D 401/06
[52] U.S. Cl. ................................................... 546/176
[58] Field of Search ........................................ 546/176

[56] References Cited

FOREIGN PATENT DOCUMENTS 287304 9/1915 Fed. Rep. of Germany .
313725 7/1919 Fed. Rep. of Germany .

OTHER PUBLICATIONS

Grignard, "Comptes Rendus", Bd. 138, pp. 152–154 (1904).
Org. Reactions, vol. 18, pp. 4 & 5 (1970).
Barton et al., Comp. Org. Chem., vol. 2, pp. 645 & 646 (1979).
Krauch et al., Reac. der Org. Chem., Huthia-Verlag, Heidelberg, pp. 262 & 263 (1976).
Ohnmacht et al., J. Med. Chem, 14, pp. 926–928 (1971).
Maginnity et al., JACS 73, pp. 3579 & 3780 (1951).
Ludwall et al., JACS, 53, pp. 318–319 (1931).
Org. Syn., vol. I, 2nd Ed., pp. 327–330, Wiley, N.Y., NY (1941).
Gilman, Org. Chem., p. 417, vol. 5, Wiley & Sons, N.Y., N.Y. (1938).

*Primary Examiner*—Donald G. Daus
*Assistant Examiner*—W. B. Springer
*Attorney, Agent, or Firm*—Keil & Witherspoon

[57] ABSTRACT

The present invention relates to a simplified process, which avoids organo-lithium intermediates, for the preparation of erythro-α-piperid-2-yl-2,8-bis-(trifluoromethyl)-quinolin-4-yl-methanol, wherein 2,8-bis-(trifluoromethyl)-quinoline-4-carboxylic acid or a salt thereof is reacted with a pyrid-2-yl-magnesium halide to give pyrid-2-yl-2,8-bis-(trifluoromethyl)-quinolin-4-yl ketone in the manner of a Grignard reaction, and this product is hydrogenated, in a conventional manner, to give erythro-α-piperid-2-yl-2,8-bis-(trifluoromethyl)-quinolin-4-yl-methanol.

7 Claims, No Drawings

PREPARATION OF ERYTHRO-α-PIPERID-2-yl-2,8-BIS-(TRIFLUORO-METHYL)-QUINOLIN-4-yl-METHANOL

Mefloquin, erythro-α-piperid-2-yl-2,8-bis-(trifluoromethyl)-quinolin-4-yl-methanol, a compound used to treat even chloroquin-resistant forms of malaria, has hitherto been synthesized by two methods, namely as described by C. J. Ohnmacht et al., J. Med. Chem. 14 (1971), 926–928, or as described in German Laid-Open Application DOS No. 2,806,909.

A particular disadvantage of both processes is that they entail working with n-butyl-lithium in diethyl ether/n-hexane mixtures at −70° C. When employed on an industrial scale, these processes entail substantial expenditure on safety measures, because of the great fire hazard. In addition it is expensive to maintain the low temperature, though this is essential since at higher temperatures the formation of by-products is increased.

It is an object of the present invention to provide a process of preparation of the above compound which is more easily carried out industrially.

We have found that this object is achieved and that erythro-α-piperid-2-yl-2,8-bis-(trifluoromethyl)quinolin-4-yl-methanol is obtained more simply, and without using organo-lithium intermediates, by a process wherein 2,8-bis-(trifluoromethyl)-quinoline-4-carboxylic acid or a salt thereof is reacted with a pyrid-2-yl-magnesium halide to give pyrid-2-yl-2,8-bis-(trifluoromethyl)-quinolin-4-yl ketone in the manner of a Grignard reaction, and this product is hydrogenated, in a conventional manner, to give erythro-α-piperid-2-yl-2,8-bis-(trifluoromethyl)-quinolin-4-yl-methanol.

In a preferred embodiment, the 2,8-bis-(trifluoromethyl)-quinoline-4-carboxylic acid, or a salt thereof, is prepared from 7-trifluoromethyl-isatin by reaction with 1,1,1-trifluoroacetone in the presence of a strong base, the 7-trifluoromethylisatin required as an intermediate being advantageously obtained by reacting 2-trifluoromethyl-aniline with chloral hydrate and hydroxylammonium chloride to give 2-trifluoromethyloxyimino-acetanilide, the latter being cyclized with concentrated sulfuric acid using a concentration of the acetanilide in the sulfuric acid of from 10 to 15% at from 75° to 85° C. in the course of from 30 minutes to 1 hour.

These reactions are illustrated in the two schemes below:

Scheme 1:

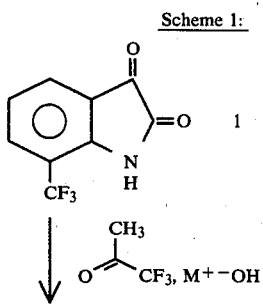

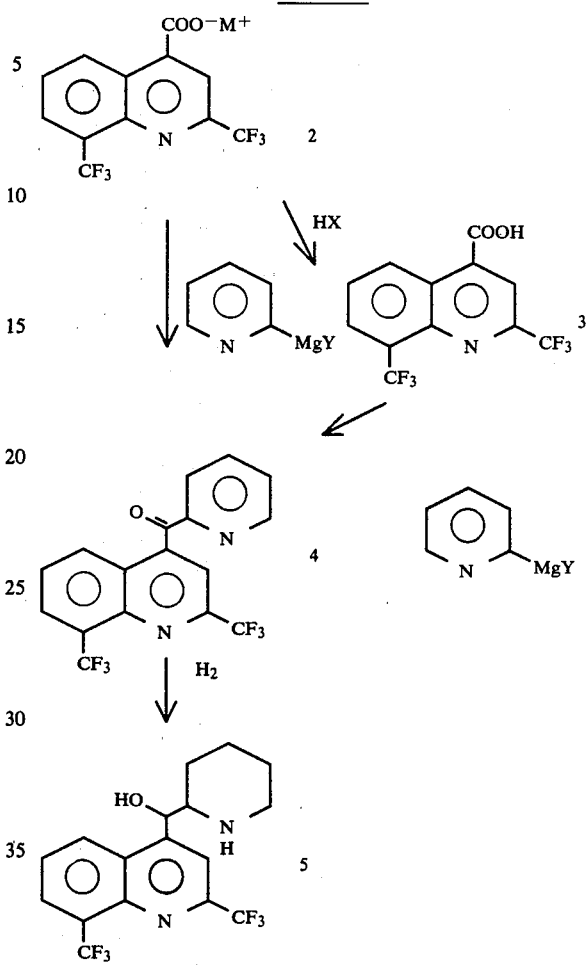

In these formulae, the preferred meanings are M=Li, Na or K, X=chlorine and Y=chlorine or bromine.

Scheme 2:

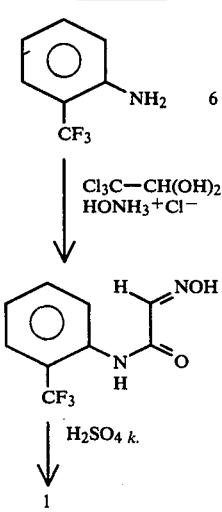

The reaction of 7-trifluoromethylisatin and 1,1,1-trifluoroacetone in amounts ranging from equimolar to 100 mole % excess is advantageously carried out in water as the solvent, in the presence of from 0 to 100 mole % excess, based on 7-trifluoromethyl-isatin, of a strong base at from 60° to 150° C., under atmospheric pressure or, if desired, in a closed system.

The preferred strong bases are the alkali metal hydroxides, especially lithium hydroxide, sodium hydroxide or potassium hydroxide, the preferred molar ratio of 7-trifluoromethyl-isatin to 1,1,1-trifluoroacetone to alkali metal hydroxide being 1:1–1.2:1–1.2. The preferred temperature range is from 60° to 150° C. The reaction can be carried out above 100° C., in a pressure vessel.

It is interesting that the reaction can advantageously be carried out at from 80° to about 100° C. under atmospheric pressure, even though the boiling point of the 1,1,1-trifluoroacetone employed is 21° C., according to J. Amer. Chem. Soc. 69 (1947), 1819. As a rule, the reaction is complete within from 1 to 20, preferably from 3 to 10, hours.

The working up of the reaction mixture is carried out in a conventional manner, by evaporating the mixture, if appropriate under reduced pressure. If the free carboxylic acid is to be prepared, the reaction mixture is acidified with a strong acid, for example with aqueous hydrochloric acid or sulfuric acid, to a pH of from 3 to 1, and the precipitate formed is isolated. If desired, a salt can be prepared directly from the free carboxylic acid and is then obtained in a particularly pure form.

It is to be pointed out that a somewhat similar reaction for the preparation of 2-substituted quinoline-4-carboxylic acids is described in, for example, J. pract. Chem., 56 (1987), 283–285 and in J. Amer. Chem. Soc., 53 (1931), 318 et seq. According to this prior art, a very large excess of alkali, namely from 4 to 9 times the calculated amount, is required, and the reaction is carried out in homogeneous solution, for example by addition of ethanol as a solubilizing agent, in order to achieve optimum results. Surprisingly, the reaction which we have described above is preferably carried out with only from 0 to 20 mole % of excess alkali, and without a solubilizing agent. If the reaction is carried out in a solvent mixture of water with ethanol or tetrahydrofuran it in fact gives unsatisfactory yields.

The 2,8-bis-(trifluoromethyl)-quinoline-4-carboxylic acid obtained, or one of its salts, is then reacted, advantageously in a cyclic saturated ether or in an aliphatic dialkyl ether or an alkoxyalkyl ether, with a pyrid-2-yl-magnesium halide in a molar ratio of from 1:2 to 1:8 at from 0° to 80° C.

The preferred pyrid-2-yl-magnesium halide is the bromide. Advantageous solvents or suspending agents to be used for the carboxylic acid or its salts include tetrahydrofuran, diethyl ether, diisopropyl ether, methyl tert.-butyl ether, ethylene glycol dimethyl ether and diethylene glycol dimethyl ether. These ethers can contain co-solvents which are inert under the reaction conditions, for example toluene or hexane.

The preferred salts for the above reaction are the alkali metal salts, especially the lithium, sodium and potassium salt, and the magnesium salt.

The preferred ratios for the reaction are, in the case of the free carboxylic acid, from 1 mole of carboxylic acid to 4 to 8 moles of the 2-bromopyridine employed to form the Grignard compound, and from 2 to 4 moles/mole in the case of the reaction of a salt of the carboxylic acid, i.e., in the case of the reaction of the free carboxylic acid, from 4 to 8 moles of the 2-bromopyridine, employed in the formation of the Grignard compound, per mole of carboxlic acid, and, in the case of the reaction of a salt of the carboxylic acid, from 2 to 4 moles of the 2-bromopyridine per mole of the carboxylic acid salt.

The preferred temperatures are from 20° to 60° C. and the reaction is as a rule complete within from 0.5 to 5 hours.

We have found that an industrially particularly advantageous embodiment of the process is to prepare the pyrid-2-yl-magnesium halide from the 2-halopyridine and magnesium in the presence of the 2,8-bis-(trifluoromethyl)quinoline-4-carboxylic acid or of its salt, and react it therewith, in situ, to give the pyrid-2-yl 2,8-bis-(trifluoromethyl)-quinoline-4-yl ketone.

The pyrid-2-yl 2,8-bis-(trifluoromethyl)-quinolin-4-yl ketone is isolated from the reaction mixture by, for example, decomposing the excess Grignard compound with water or a mineral acid, with or without cooling, evaporating off the solvent and extracting the residue with an organic solvent, for example toluene or n-hexane. Advantageously, excess aqueous mineral acid, for example sulfuric acid or hydrochloric acid, is added to the residue before extraction. It is also possible to add mineral acid to the evaporation residue, then add a complexing agent for magnesium ions, for example ethylenediaminetetraacetic acid, thereafter render the mixture alkaline with an aqueous alkali, for example sodium hydroxide solution or potassium hydroxide solution, and finally extract the batch with an organic solvent, for example toluene or n-hexane. A very pure pyrid-2-yl-2,8-bis-(trifluoromethyl)-quinolin-4-yl ketone is obtained if the crude ketone is subsequently extracted by boiling with n-hexane and isolated from the n-hexane solution by evaporation and/or crystallization. The ketone obtained can be further purified by recrystallization, for example from methanol or ethanol, advantageously in the pressure of active charcoal, or by sublimation at about 100° C. bath temperature, under about 0.01–0.1 mbar.

We have found, surprisingly, that a very advantageous method of working up is to evaporate the Grignard reaction mixture directly, dissolve the evaporation residue in a relatively concentrated acid, especially concentrated hydrochloric acid, from 1 to 3 parts of aqueous concentrated hydrochloric acid being used per part of evaporation residue, filter the solution if necessary, and then precipitate the pyrid-2-yl-2,8-bis-(trifluoromethyl)-quinolin-4-yl ketone by dilution with water, from 1 to 10 parts of water being used per part of the acid employed.

This procedure virtually completely removes impurities which are otherwise difficult to remove and which are detectable in a thin layer chromatogram (Merck prepared silica gel plates 60 F 254; mobile phase; the upper phase of a previously well-stirred mixture of 5 parts by volume of toluene, 5 parts by volume of glacial acetic acid and one part by volume of water) by the spots which remain in the proximity of the starting point and give an intense brown color with iodine vapor.

The purification process described can advantageously also be used to obtain the above ketone, in a pure form, from heavily contaminated residues.

The hydrogenation of the ketone to give erythro-α-piperid-2-yl-2,8-bis-(trifluoromethyl)-quinolin-4-yl-methanol is carried out in a conventional manner, as described, for example, in the two publications mentioned earlier, eg. over a platinum catalyst, in alcoholic hydrochloric acid. The Mefloquin is thereby obtained in the form of its hydrochloride.

The 7-trifluoromethylisatin required for the process according to the invention may be prepared particularly advantageously by reacting o-trifluoromethylaniline with chloral hydrate and hydroxylammonium chloride in a molar ratio of 1:1.45:4.1 in an aqueous hydrochloric acid solution of sodium sulfate, containing from 2.5 to 3.5% by weight of o-trifluoromethylaniline, from 0.6 to 0.8% by weight of hydrogen chloride and from 17 to 25% by weight of sodium sulfate decahydrate, at from 50° to 100° C., preferably from 70° to 90° C., and cyclizing the 2-trifluoromethyloximinoacetanilide, obtained directly in a crystalline form from the reaction mixture, in 10–15% strength by weight solution in concentrated sulfuric acid at from 75° to 85° C. in the course of from ½ to 1 hour.

These reactions are known in principle, for example from J. Amer. Chem. Soc., 73 (1951), 3579–80 and from a similar method for the preparation of isatin given in Org. Synth. Coll. Volume I (1941), 327–330. However, under the specific conditions used, in particular that an excess of chloral hydrate is employed, that the reaction temperature is lowered to 80° C. and that the reaction is carried out in a more dilute solution and with a lower concentration of sodium sulfate, the yield is improved from 64 to about 80%. In addition to the improvement in yield, and the fact that lower temperatures and lower amounts of sodium sulfate are employed, the extraction with an organic solvent is also dispensed with. The same is true of the cyclization reaction to give 7-tri-fluoromethyl-isatin, where the deliberate measures taken are in particular to carry out the cyclization in dilute solution for a relatively long reaction time, at an elevated temperature, thereby obtaining a substantially improved yield of almost 80% compared to the 60% achieved in the prior art. These advantages, which are particularly important for industrial manufacture, are all the more noteworthy since the process is carried out in a temperature range which according to the literature (J. Amer. Chem. Soc., 73 (1951), 3579 and J. Org. Synth. Coll. Volume I (1941), 329) would be expected to lead to a substantial reduction in yield.

In the Examples, parts bear the same relation to parts by volume as that of the kilogram to the liter.

EXAMPLE 1

2,8-Bis-(trifluoromethyl)-quinoline-4-carboxylic acid

A mixture of 100 parts by volume of water, 9.6 parts of sodium hydroxide, 43 parts of 7-trifluoromethylisatin and 26.8 parts of 1,1,1-trifluoroacetone is boiled for 6 hours, under atmospheric pressure, in a reaction vessel equipped with a stirrer, condenser, internal thermometer and feed device. The thin layer chromatogram of a sample taken after this reaction time and worked up with acid no longer shows any 7-trifluoromethyl-isatin. The batch is then allowed to cool, and 2 N hydrochloric acid is added, whilst stirring, until the pH is 2.5. The product which precipitates is washed with water and dried. 57 parts of 2,8-bis-(trifluoromethyl)-quinoline-4-carboxylic acid, ie. 92.2% of theory, are obtained.

EXAMPLE 2

2,8-Bis-(trifluoromethyl)-quinoline-4-carboxylic acid

The procedure described in Example 1 is followed, except that the reaction mixture is heated for 25 hours at 70° C. After working up as in Example 1, 52 parts of 2,8-bis-(trifluoromethyl)-quinoline-4-carboxylic acid, ie. 84.1% of theory, are obtained.

EXAMPLE 3

2,8-Bis-(trifluoromethyl)-quinoline-4-carboxylic acid

A mixture of 100 parts by volume of water, 5.01 parts of lithium hydroxide, 43 parts of 7-trifluoromethylisatin and 23.5 parts of 1,1,1-trifluoroacetone is heated for 5 hours, as described in Example 1. After working up as in Example 1, 55 parts of 2,8-bis-(trifluoromethyl)quinoline-4-carboxylic acid, ie. 89.0% of theory, are obtained.

EXAMPLE 4

2,8-Bis-(trifluoromethyl)-quinoline-4-carboxylic acid

A mixture of 100 parts by volume of water, 5.7 parts of lithium hydroxide, 43 g of 7-trifluoromethylisatin and 26.8 g of 1,1,1-trifluoroacetone is heated, and stirred, for 5 hours at 110° C. in a metal autoclave equipped with a stirrer and internal thermometer. After working up as described in Example 1, 56 parts of 2,8-bis-(trifluoromethyl)-quinoline-4-carboxylic acid, ie. 90.6% of theory, are obtained.

EXAMPLE 5

2,8-Bis-(trifluoromethyl)-quinoline-4-carboxylic acid

The procedure followed is as described in Example 4, except that 12.2 parts of potassium hydroxide are employed instead of lithium hydroxide, and the mixture is heated for 15 hours at 90° C. After working up as in Example 4, 58 parts of 2,8-bis-(trifluoromethyl)-quinoline-4-carboxylic acid, ie. 93.8% of theory, are obtained.

COMPARATIVE EXAMPLE FOR EXAMPLE 5

2,8-Bis-(trifluoromethyl)-quinoline-4-carboxylic acid

The procedure described in Example 5 is followed, except that in place of pure water a mixture of 50 parts by volume of water and 50 parts by volume of ethanol is used. After working up, 43 1 parts of 2,8-bis-(trifluoromethyl)-quinoline-4-carboxylic acid, ie. 69.6% of theory, are obtained.

EXAMPLE 6

2,8-Bis-(trifluoromethyl)-quinoline-4-carboxylic acid

A mixture of 100 parts by volume of water, 8.8 parts of sodium hydroxide, 43.2 parts of 7-trifluoromethyl-isatin and 27.4 parts of 1,1,1-trifluoroacetone is heated for 8 hours at 110° C. in an autoclave. When the mixture has cooled, 2 N hydrochloric acid is added, whilst stirring, until the pH has reached 2.7 and the precipitate formed is filtered off and dried at 70° C. and about 20 mbar. 60 parts of 2,8-bis-(trifluoromethyl)-quinoline-4-carboxylic acid, ie. 97.1% of theory, are obtained.

EXAMPLE 7

Pyrid-2-yl-2,8-bis-(trifluoromethyl)-quinolin-4-yl ketone 14.6 parts of magnesium filings and 200 parts by volume of tetrahydrofuran are first introduced into the reactor, under argon. The mixture is heated to 50°–58° C., about 0.05 part of iodine and about 1 part by volume of carbon tetrachloride are added and the mixture is stirred until the brown color of the iodine has almost disappeared. A solution of 32 parts of 2-bromopyridine in 30 parts by volume of tetrahydrofuran is then added at from 50° to 60° C. and after completion of the addition the mixture is stirred for a further 30 minutes, at 50°

C. The solution, which has turned dark, is decanted from the residual undissolved magnesium, and is added in the course of about 10 minutes, under argon, to a stirred suspension of 20 parts of the lithium salt of 2,8-bis-(trifluoromethyl)-quinoline-4-carboxylic acid in 100 parts by volume of tetrahydrofuran; during the addition, the temperature of the reaction mixture rises from 24° to 40° C. After 30 minutes' stirring, 2,8-bis-(trifluoromethyl)-quinoline-4-carboxylic acid is no longer detectable in the thin layer chromatogram of a sample which has been worked up with acid. The solvent is then distilled off, the residue is taken up in a mixture of 500 parts by volume of water and 150 parts by volume of 2 N hydrochloric acid, 148 parts of ethylenediaminetetraacetic acid, for example in the form of Titriplex III ®, are added to the solution, the pH is brought to about 12 by adding concentrated sodium hydroxide solution, and the resulting solution is extracted continuously for about 3 hours with 2,000 parts by volume of toluene in a percolator, after which the toluene extract is evaporated. 21 parts of crude pyrid-2-yl-2,8-bis-(trifluoromethyl)-quinolin-4-yl ketone are obtained, corresponding to 89.4% of theory. 15.6 parts of pure pyrid-2-yl-2,8-bis-(trifluoromethyl)-quinolin-4-yl ketone, ie. 66.4% of theory, may be isolated by twice extracting the crude ketone by boiling with 500 parts by volume of n-hexane at a time.

EXAMPLE 8

Pyrid-2-yl-2,8-bis-(trifluoromethyl)-quinolin-4-yl ketone

The procedure described in Example 7 is followed, but after starting the Grignard reaction the solution of 2-bromopyridine in tetrahydrofuran is added at 30°–35° C., so that the reaction does not stop, and the resulting Grignard solution is reacted with a suspension of 22.05 parts of the potassium salt of 2,8-bis-(trifluoromethyl)-quinoline-4-carboxylic acid in 70 parts by volume of 1,2-dimethoxy-ethane. After working up as in Example 7, 20 parts of crude pyrid-2-yl-2,8-bis-(trifluoromethyl)-quinolin-4-yl ketone, ie. 85.1% of theory, are obtained. The treatment with n-hexane gives 14.8 parts of pure ketone, ie. 63.0% of theory.

EXAMPLE 9

Pyrid-2-yl-2,8-bis-(trifluoromethyl)-quinolin-4-yl ketone

The procedure described in Example 7 is followed, but the residue (81 parts) obtained by distilling off the solvent after completion of the reaction is dissolved in 200 parts of concentrated hydrochloric acid, insoluble constituents are filtered off, and the product is precipitated by stirring the solution into 700 parts of water, and is filtered off and dried. 19.3 parts of pure pyrid-2-yl-2,8-bis-(trifluoromethyl)-quinolin-4-yl ketone, ie. 82.1% of theory, are obtained.

Pyrid-2-yl-2,8-bis-(trifluoromethyl)-quinolin-4-yl ketone

The procedure described in Example 7 is followed, but instead of the lithium salt 9.45 parts of the free 2,8-bis-(trifluoromethyl)-quinoline-4-carboxylic acid are employed in the reaction. After working up, 8.1 parts of crude pyrid-2-yl-2,8-bis-(trifluoromethyl)-quinolin-4-yl ketone, ie. 73.0% of theory, are obtained. After the treatment with n-hexane, 5.9 parts of pure ketone, ie. 52.1% of theory, are obtained.

EXAMPLE 11

Pyrid-2-yl-2,8-bis-(trifluoromethyl)-quinolin-4-yl ketone

The procedure described in Example 7 is followed, except that 20 parts of the lithium salt of 2,8-bis-(trifluoromethyl)-quinoline-4-carboxylic acid in 100 parts by volume of diethyl ether in place of tetrahydrofuran are employed. 23 g of crude pyrid-2-yl-2,8-bis-(trifluoromethyl)-quinolin-4-yl ketone, ie. 97.9% of theory, are obtained. Extracting this product by boiling with n-hexane gives 17.3 parts of pure ketone, ie. 73.6% of theory.

EXAMPLE 12

Pyrid-2-yl-2,8-bis-(trifluoromethyl)-quinolin-4-yl ketone

The reaction is carried out as described in Example 11 and the residue obtained after evaporating the reaction mixture is worked up as described in Example 9. 18.1 parts of pure pyrid-2-yl-2,8-bis-(trifluoromethyl)-quinolin-4-yl ketone, ie. 81.5% of theory, are obtained.

EXAMPLE 13

Pyrid-2-yl-2,8-bis-(trifluoromethyl)-quinolin-4-yl ketone 3.2 parts of sodium hydroxide are added to 24 parts of 2,8-bis-(trifluoromethyl)-quinoline-4-carboxylic acid in 100 parts by volume of water. After evaporation and drying, the sodium salt of 2,8-bis-(trifluoromethyl)-quinoline-4-carboxylic acid is obtained in quantitative yield.

10.9 parts of magnesium and 24 parts of 2-bromopyridine in 170 parts by volume of tetrahydrofuran are reacted, similarly to Example 7, to give pyrid-2-yl-magnesium bromide, which is then reacted, similarly to Example 7, with 16 parts of the abovementioned sodium salt, suspended in 80 parts by volume of diethyl ether. After working up, 12 parts of crude pyrid-2-yl-2,8-bis-(trifluoromethyl)-quinolin-4-yl ketone, ie. 76.1% of theory, are obtained.

COMPARATIVE EXAMPLE FOR EXAMPLE 13

Pyrid-2-yl-2,8-bis-(trifluoromethyl)-quinolin-4-yl ketone

The procedure described in Example 6 is followed, but the reaction mixture is worked up by evaporation, to give the sodium salt of 2,8-bis-(trifluoromethyl)-quinoline-4-carboxylic acid. The crude sodium salt (58 parts), which still contains excess sodium hydroxide, has the following composition (the calculated analytical values for the pure sodium salt being given in brackets):

C: 42.0% (43.5%)
H: 1.5% (1.2%)
F: 33.1% (34.4%)
N: 4.4% (4.2%)
Na: 8.0% (6.9%)

Following the method described in Example 13, a Grignard reagent is prepared from 17.4 parts of magnesium filings and 38.4 parts of 2-bromopyridine in 200 parts by volume of tetrahydrofuran and reacted with 21.2 parts of the crude sodium salt described above, suspended in 120 parts by volume of diethyl ether. After working up, 16 parts of crude pyrid-2-yl-2,8-bis-(trifluoromethyl)-quinolin-4-yl ketone, ie. 74.3% of theory, are obtained. Extracting this crude material by boiling with n-hexane gives 13.7 parts of pure ketone, ie. 63.6% of theory.

EXAMPLE 14

Pyrid-2-yl-2,8-bis-(trifluoromethyl)-quinolin-4-yl ketone

The reaction is carried out as described in Example 13 and the residue obtained by evaporation after the reaction is worked up as described in Example 9. 12.5 parts of pure pyrid-2-yl-2,8-bis-(trifluoromethyl)-quinolin-4-yl ketone, ie. 70.4% of theory, are obtained.

EXAMPLE 15

Pyrid-2-yl-2,8-bis-(trifluoromethyl)-quinolin-4-yl ketone

Using a similar method to Example 1, 12.2 parts of potassium hydroxide, 43 parts of 7-trifluormethyl-isatin and 26.8 parts of 1,1,1-trifluoroacetone, in 100 parts by volume of water, are reacted under atmospheric pressure for 6 hours at about 95° C. The reaction solution is then evaporated and after drying the residue for 36 hours at 130° C. under about 20 mbar, 65 parts of the crude potassium salt of 2,8-bis-(trifluoromethyl)-quinoline-4-carboxylic acid, still containing excess KOH, are obtained; this product has the following composition (the calculated analytical values for the pure potassium salt being given in brackets):

C: 41.0% (41.5%)
H: 1.4% (1.2%)
F: 32.2% (32.8%)
K: 11.0% (11.3%)
N: 4.4% (4.0%)

Using a similar method to Example 7, a Grignard reagent is prepared from 14.6 parts of magnesium filings and 32 parts of 2-bromopyridine in 230 parts by volume of tetrahydrofuran, and is reacted with 22.3 parts of the above crude potassium salt, suspended in 100 parts by volume of diethyl ether. After working up (by dissolving the evaporation residue from the Grignard reaction in a mixture of 500 parts by volume of water and 100 parts by volume of concentrated hydrochloric acid, adding 100 parts of ethylenediaminetetraacetic acid, bringing the pH to 12 with 50% strength sodium hydroxide solution, continuously extracting the mixture with 2,000 parts by volume of toluene in a precolator and evaporating the toluene extract), 19.5 parts of crude pyrid-2-yl-2,8-bis-(trifluoromethyl)-quinolin-4-yl ketone, ie. 76.8% of theory, are obtained. After extraction by boiling twice with 800 parts by volume of n-hexane at a time, 14.9 parts of pure ketone, ie. 58.7% of theory, are isolated.

EXAMPLE 16

Pyrid-2-yl-2,8-bis-(trifluoromethyl)-quinolin-4-yl ketone 2.45 parts of magnesium filings are introduced, under argon, into an apparatus equipped with a stirrer and internal thermometer, after which one part by volume of a solution of 11.5 parts of 2-chloropyridine in 24 parts by volume of tetrahydrofuran is added. After starting the Grignard reaction by adding 0.2 part by volume of ethyl bromide, the remainder of the 2-chloropyridine solution is added in the course of 15 minutes, while stirring. During this addition, the reaction mixture rises to the boil and turns dark. A further 30 parts by volume of tetrahydrofuran are added over 50 minutes, and the reaction mixture is kept at the boil for a total of 3 hours.

The viscous product is decanted from residual undissolved magnesium under an inert gas blanket and is added dropwise, with thorough stirring, to 9.5 parts of the lithium salt of 2,8-bis-(trifluoromethyl)-quinoline-4-carboxylic acid, in 100 parts by volume of tetrahydrofuran, at 50° C.; the mixtue is then stirred for a further 2 hours at the same temperature.

After working up in the same manner as in Example 15, 5 parts of crude pyrid-2-yl-2,8-bis-(trifluoromethyl)-quinolin-4-yl ketone, ie. 44.8% of theory, are obtained. Extraction of this product by boiling with n-hexane gives 3 parts of pure ketone, ie. 26.9% of theory.

EXAMPLE 17

Pyrid-2-yl-2,8-bis-(trifluoromethyl)-quinolin-4-yl ketone 24.9 parts of thallium-(I) ethylate are added to 31 parts of 2,8-bis-(trifluoromethyl)-quinoline-4-carboxylic acid in 200 parts by volume of absolute ethanol. After evaporation and drying, 51 parts of the thallium-(I) salt of 2,8-bis-(trifluoromethyl)-quinoline-4-carboxylic acid are obtained.

16.4 parts of magnesium and 32 parts of 2-bromopyridine in 200 parts by volume of tetrahydrofuran are reacted, by a method similar to Example 7, to give pyrid-2-yl-magnesium bromide. The resulting solution of the Grignard reagent is decanted from excess magnesium and added dropwise, under argon, to a well-stirred solution of 33 parts of the above thallium salt in 100 parts by volume of tetrahydrofuran, whilst cooling the mixture externally to ensure that the internal temperature does not exceed 45° C. After working up as described in Example 7, 17 parts of crude pyrid-2-yl-2,8-bis-(trifluoromethyl)-quinolin-4-yl ketone, ie. 71.3% of theory, are obtained; extracting this material by boiling with n-hexane gives 15.2 parts of pure ketone, ie. 63.8% of theory.

EXAMPLE 18

Pyrid-2-yl-2,8-bis-(trifluoromethyl)-quinolin-4-yl ketone

A mixture of 4.1 parts of magnesium, 24 parts of 2-bromopyridine, 20 parts of the lithium salt of 2,8-bis-(trifluoromethyl)-quinoline-4-carboxylic acid, 0.05 part of iodine and 1 part by volume of carbon tetrachloride is heated to 60° C. under argon, whilst stirring; the reaction starts readily, and the mixture is then stirred further for one hour at 50° C. Thereafter the solution is decanted from undissolved material, mixed with 5 parts by volume of water and evaporated. The evaporation residue (64 parts) is dissolved in 200 parts by volume of concentrated hydrochloric acid and the resulting solution is diluted with 1,500 parts by volume of water, whilst stirring. The precipitate thus formed is filtered off, washed with water and dried. 14 parts of pure pyrid-2-yl-2,8-bis-(trifluoromethyl)-quinolin-4-yl ketone, ie. 59.6% of theory, are obtained.

EXAMPLE 19

Erythro-α-piperid-2-yl-2,8-bis-(trifluoromethyl)-quinolin-4-yl-methanol

A mixture of 1,400 parts by volume of 95% strength ethanol, 7.6 parts of 37% strength hydrochloric acid and 25 parts of a hydrogenation catalyst (from Engelhard Inds.), containing 5% of platinum on active charcoal, is introduced into a hydrogenation apparatus equipped with a stirrer and internal thermometer, and is saturated with hydrogen. A solution of 25 parts of pyrid-2-yl-2,8-bis-(trifluoromethyl)-quinolin-4-yl ketone in 200 parts by volume of 95% strength ethanol is then added and the hydrogenation is carried out at 24° C. under atmospheric pressure, with the stirrer running at 800 rpm. When, after 15 hours, 6,600 parts by volume of hydrogen have been taken up, corresponding to 4.01 moles of hydrogen per mole of pyrid-2-yl-2,8-bis-(trifluoromethyl)-quinolin-4-yl ketone, the hydrogenation is discontinued. The solution is filtered to remove the catalyst and is evaporated, giving 26.5 parts of crude erthro-α-piperid-2-yl-2,8-bis-(trifluoromethyl)-quinolin-4-yl-methanol hydrochloride, ie. 94.6% of theory.

EXAMPLE 20

2-Trifluoromethyl-oximinoacetanilide

A mixture of 87 parts of o-trifluoromethylaniline, 3,000 parts of water, 600 parts of sodium sulfate decahydrate, 54 parts of concentrated hydrochloric acid, 130 parts of chloral hydrate and 154 parts of hydroxylammonium chloride is stirred for 20 minutes, at 80° C., in a reaction vessel equipped with a stirrer, reflux condenser and internal thermometer. As the mixture cools to room temperature, an oil first separates out, and then crystallizes completely on continued stirring. The crystals are separated from the mother liquor and dried. 100 parts of 2-trifluoromethyl-oximinoacetanilide, ie. 79.8% of theory, are obtained.

EXAMPLE 21

7-Trifluoromethyl-isatin 110 parts of 2-trifluoromethyloximinoacetanilide are introduced, a little at a time, into 500 parts by volume of concentrated sulfuric acid at 80° C., with vigorous stirring. This temperature is then maintained for 30 minutes, after which the reaction mixture is cooled to room temperature and poured onto about 4,000 parts of ice. The precipitate formed is filtered off, washed with water and dried at 40° C. under reduced pressure from a water pump. 80 parts of 7-trifluoromethyl-isatin, ie. 78.5% of theory, are obtained.

We claim:

1. A process for the preparation of erythro-α-piperid-2-yl-2,8-bis-(trifluoromethyl)-quinolin-4-yl-methanol which comprises the steps of reacting 2,8-bis-(trifluoromethyl)-quinoline-4-carboxylic acid or a salt thereof with a pyrid-2-yl-magnesium halide in a cyclic saturated ether or in an aliphatic dialkyl ether or an alkoxyalkyl ether in a molar ratio of from 1:2 to 1:8 at from 0° to 80° C. to give pyrid-2-yl 2,8-bis-(trifluoromethyl)-quinolin-4-yl ketone and the latter is hydrogenated in a conventional manner to give erythro-α-piperid-2-yl-2,8-bis-(trifluoromethyl)-quinolin-4-yl-methanol.

2. The process of claim 1, wherein the lithium, sodium, potassium or magnesium salt of 2,8-bis-(trifluoromethyl)-quinoline-4-carboxylic acid is used.

3. The process of claim 1, wherein pyrid-2-yl-magnesium bromide is used.

4. The process of claim 1, wherein, in the reaction of 2,8-bis-(trifluoromethyl)-quinoline-4-carboxylic acid with the pyrid-2-yl-magnesium halide, the molar ratio of the pyrid-2-yl halide employed in preparing the Grignard compound to the carboxylic acid is 4–8:1, whilst if the carboxylic acid is employed in the form of a salt, the corresponding molar ratio is 2–4:1.

5. The process of claim 1, wherein the Grignard reaction is carried out in tetrahydrofuran, diethyl ether, diisopropyl ether, 1,2-dimethoxyethane, diethylene glycol dimethyl ether or methyl tert.-butyl ether or a mixture of these ethers.

6. The process of claim 1, wherein the pyrid-2-yl-magnesium halide is prepared in the presence of the 2,8-bis-(trifluoromethyl)-quinoline-4-carboxylic acid or of a salt thereof, and is reacted in situ with the said carboxylic acid or salt thereof.

7. The process of claim 1, wherein the mixture from the Grignard reaction is evaporated direct, the evaporation residue is dissolved in aqueous concentrated hydrochloric acid, using from 1 to 3 parts of acid per part of residue, the solution is filtered if necessary, and the pyrid-2-yl-2,8-bis-(trifluoromethyl)-quinolin-4-yl ketone is then precipitated by dilution with water, using from 1 to 10 parts of water per part of concentrated hydrochloric acid.

* * * * *